(12) United States Patent
Agrawal et al.

(10) Patent No.: US 7,803,393 B2
(45) Date of Patent: Sep. 28, 2010

(54) PREPARING AN IMPLANT BY GAS-PLASMA TREATMENT OF A SUBSTRATE TO COUPLE CELLS

(75) Inventors: C. Mauli Agrawal, San Antonio, TX (US); Steven R. Bailey, San Antonio, TX (US); Jodie L. Polan, San Antonio, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 74 days.

(21) Appl. No.: 10/506,956

(22) PCT Filed: Mar. 6, 2003

(86) PCT No.: PCT/US03/06942

§ 371 (c)(1),
(2), (4) Date: Mar. 24, 2005

(87) PCT Pub. No.: WO03/075790

PCT Pub. Date: Sep. 18, 2003

(65) Prior Publication Data

US 2005/0163816 A1 Jul. 28, 2005

(51) Int. Cl.
*A61F 2/00* (2006.01)
*C12N 11/08* (2006.01)
*C12N 5/07* (2006.01)

(52) U.S. Cl. .................. 424/423; 424/93.7; 435/180; 435/396; 435/397

(58) Field of Classification Search ........................ None
See application file for complete search history.

(56) References Cited

U.S. PATENT DOCUMENTS

| | | | |
|---|---|---|---|
| 3,814,983 A | 6/1974 | Weissfloch et al. ............ 315/39 |
| 4,927,676 A | 5/1990 | Williams et al. .............. 428/36 |
| 4,929,319 A | 5/1990 | Dinter et al. ................. 204/164 |
| 4,948,628 A | 8/1990 | Montgomery et al. ......... 427/39 |
| 5,034,265 A | 7/1991 | Hoffman et al. ............ 428/253 |
| 5,055,316 A | 10/1991 | Hoffman et al. ................ 427/2 |
| 5,080,924 A | 1/1992 | Kamel et al. ................... 427/2 |
| 5,084,151 A | 1/1992 | Vallana et al. ......... 204/192.11 |
| 5,217,743 A | 6/1993 | Farah ............................. 427/2 |
| 5,229,172 A | 7/1993 | Cahalan et al. ............. 427/536 |
| 5,236,563 A | 8/1993 | Loh ............................ 204/165 |
| 5,246,451 A | 9/1993 | Trescony et al. ................ 623/1 |
| 5,260,093 A | 11/1993 | Kamel et al. .................... 427/2 |
| 5,262,097 A | 11/1993 | Christ et al. .................. 264/1.4 |
| 5,364,662 A | 11/1994 | Domenico et al. ........... 427/536 |
| 5,451,428 A | 9/1995 | Rupp ......................... 427/2.12 |
| 5,476,509 A | 12/1995 | Keogh et al. .................... 623/1 |
| 5,543,019 A | 8/1996 | Lee et al. ................ 204/192.15 |
| 5,580,779 A * | 12/1996 | Smith et al. .................. 435/378 |
| 5,702,446 A | 12/1997 | Schenck et al. ................ 623/16 |
| 5,741,329 A | 4/1998 | Agrawal et al. ................ 623/11 |
| 5,836,949 A | 11/1998 | Campbell, Jr. et al. ......... 606/62 |
| 5,840,387 A * | 11/1998 | Berlowitz-Tarrant et al. ........................ 428/36.91 |
| 5,876,446 A | 3/1999 | Agrawal et al. ................ 623/11 |
| 5,947,893 A | 9/1999 | Agrawal et al. ................ 600/36 |
| 6,033,582 A | 3/2000 | Lee et al. ........................ 216/37 |
| 6,065,476 A | 5/2000 | Agrawal et al. .............. 128/898 |
| 6,087,331 A * | 7/2000 | Newman et al. ............... 514/12 |
| 6,187,329 B1 | 2/2001 | Agrawal et al. .............. 424/426 |
| 6,255,359 B1 | 7/2001 | Agrawal et al. ................ 521/64 |
| 6,306,615 B1 * | 10/2001 | Beckmann et al. ............. 435/7.2 |
| 6,419,920 B1 * | 7/2002 | Mineau-Hanschke .... 424/93.21 |
| 6,447,768 B1 * | 9/2002 | van Zonneveld et al. ... 424/93.2 |
| 6,582,391 B2 * | 6/2003 | Mineau-Hanschke ........ 604/19 |

OTHER PUBLICATIONS

PCT, "International Search Report" for International Application No. PCT/US03/06942, mailed Nov. 26, 2003; 6 pages.
Bailey et al. "Proliferation and b-tubulin for human aortic endothelial cells within gas-plasma scaffolds" 2004 Cardiovascular Radiation Medicine, vol. 5, pp. 119-124.
Bailey et al., "Angiogenic bFGF expression from gas-plasma treated scaffolds" 2002, Cardiovascular Radiation Medicine vol. 3 pp. 183-189.
Polan et al., "VEGF analysis induced by endothelialized gas-plasma treated D,L-PLA scaffolds" 2002 Cardiovascular Radiation Medicine vol. 3 pp. 176-182.

\* cited by examiner

*Primary Examiner*—David M Naff
(74) *Attorney, Agent, or Firm*—Meyertons, Hood, Kivlin, Kowert & Goetzel, P.C.; Eric B. Meyertons

(57) ABSTRACT

An implant for use in biological/biomedical applications may be prepared by subjecting a substrate to a gas-plasma treatment. The substrate may be a biocompatible material, including metals, ceramics, and polymers. More specifically, the substrate may be a bioresorbable polymer. The gas-plasma treatment may include subjecting the substrate to a plasma formed by a reactive gas. The gas-plasma treatment may be performed for a chosen duration at a radio frequency within a temperature range, a pressure range, and a supplied energy range. The substrate may be exposed to living cells, such that some of the living cells become coupled to the substrate. Gas-plasma treatment parameters may be chosen such that the living cells coupled to the treated substrate produce more of a cellular product than living cells coupled to an untreated substrate.

12 Claims, 2 Drawing Sheets

PREPARING AN IMPLANT BY GAS-PLASMA TREATMENT OF A SUBSTRATE TO COUPLE CELLS

BACKGROUND OF THE INVENTION

1. Field of the Invention

The invention generally relates to gas-plasma treatment of substrates. More specifically, the invention relates to preparing an implant for use in biological/biomedical applications by subjecting the substrate to a gas-plasma treatment.

2. Description of Related Art

Successful repair or replacement of damaged or diseased tissues, organs, or bones requires integration of donor tissue or an implant with a patient's body. While tissue from the patient or from another donor may be integrated more readily than an implant, tissue transplantation has a high rate of failure and is accompanied by a risk of disease transmission. In addition, donor tissue may be in short supply, and transplantation procedures may be expensive. Implants used as medical implants have therefore been increasingly investigated as alternatives to donor tissue.

Although implants circumvent some of the problems associated with donor tissue, the use of implants introduces other problems. An artificial or synthetic implant may be incompatible with the body and may not function as well as the original tissue. Since the surface properties of an implant generally govern the interaction of the implant with the body, rejection and other medical complications are often traced to incompatible implant surfaces. Inert implants, once thought to be desirable, are now known to cause surrounding growth of fibrous tissue, thereby inhibiting integration of the implant with a patient's body. Biocompatible implants are believed to reduce this and other adverse membrane-mediated cellular responses, such as infection, inflammation, blood coagulation, etc., related to the presence of foreign matter in the body. Thus, considerable attention has been directed toward increasing biocompatibility of implants through modification of implant surfaces to mimic functionally equivalent surfaces in the body.

Implants are typically made from metals, polymers, and ceramics. These materials, however, do not generally adhere to host tissue or coatings designed to enhance implant biocompatibility. Therefore, implant surfaces are often conditioned or treated to increase adhesion to the host tissue or to a desired coating composition. A purpose of such treatment is to enhance integration of an implant with adjacent host tissue. Successful surface modification results in an implant with surface characteristics that allow adhesion of a desired coating. Implants thus treated allow ingrowth, or integration of host tissue with the implant coating.

A goal of forming biocompatible implants is choosing the most effective treatment and coating for the intended application. Coatings typically include inorganic, polymeric, and biological coatings. Since endothelial cells form blood-surface interfaces in the human body, the attachment of endothelial cells to implant surfaces as a method of promoting integration of the implant and inhibiting adverse membrane-mediated cell responses of the host tissue has been studied.

U.S. Pat. No. 6,033,582 to Lee et al., which is incorporated by reference as if fully set forth herein, describes gas-plasma treatment of implant device surfaces to obtain desirable surface features that enhance and optimize adhesion of coating materials and/or tissue interactions with the surface of a medical implant device.

An improvement in implant technology involves using implants as a source of drugs, agents, or other active substances, such as growth factors, to assist in wound healing and aid ingrowth of host tissue. Although controlled release of a therapeutic substance has received some interest, these applications typically involve the immediate, unsustained release of the therapeutic substance.

SUMMARY OF THE INVENTION

An implant for use in biological/biomedical applications may be prepared by subjecting a substrate to a gas-plasma treatment. The substrate may be a biocompatible material, including metals, ceramics, and polymers. More specifically, the substrate may be a bioresorbable polymer, such as a polylactide. The substrate may be a planar solid or a nonplanar solid. In some embodiments, the substrate may be a three-dimensional matrix. In an embodiment, the implant is a medical implant.

Gas-plasma treatment of a substrate may include subjecting the substrate to a plasma formed by a reactive gas. A reactive gas may include oxygen. In an embodiment, a duration of the gas-plasma treatment may be from about 1 minute to less than about 5 minutes. During gas-plasma treatment, the substrate may be exposed to a reactive gas at a temperature of less than about 50° C. In an embodiment, a substrate is exposed to a reactive gas at a pressure between about 0.01 and 10 torr. Energy supplied to a gas-plasma chamber may be between about 5 kJ and about 10 kJ. A discharge frequency between about 10 kHz and about 100 GHz may be used in the gas-plasma treatment. In an embodiment, the discharge frequency may be between about 13 MHz and about 14 MHz.

In an embodiment, a substrate may be exposed to living cells. A portion of the living cells may become coupled to the substrate. Living cells that may be coupled to a substrate include endothelial cells, human aortic endothelial cells, muscle cells, myocardial cells, and epithelial cells. Living cells coupled to a treated substrate may produce more of a cellular product than living cells coupled to an untreated substrate. Cellular products that show an increase in production may include nucleic acids and proteins. More specifically, living cells coupled to a treated substrate may produce more of a growth factor than living cells coupled to an untreated substrate. An increase in production may be seen for growth factors including vascular endothelial growth factor, basic fibroblast growth factor, epidermal growth factor, and platelet-endothelial cell adhesion molecule-1.

In an embodiment, an implant may be implanted into a person following gas-plasma treatment of a substrate. Living cells coupled to the treated substrate may produce more of a cellular product than living cells coupled to an untreated substrate. In an embodiment, a substrate may be exposed to living cells prior to implanting the implant in a person.

BRIEF DESCRIPTION OF THE DRAWINGS

Other objects and advantages of the invention will become apparent upon reading the following detailed description and upon reference to the accompanying drawings in which.

Figure 1A:
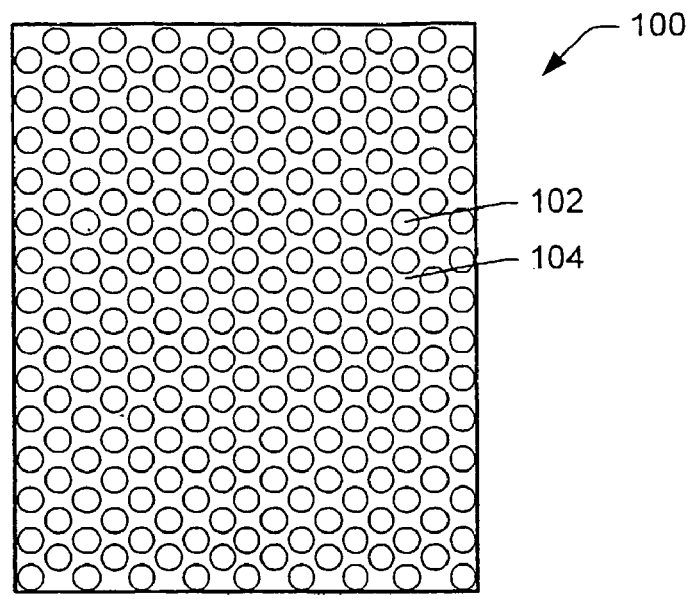
FIGS. 1A and 1B depict cross-sectional views of embodiments of a scaffold.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents, and alternatives falling within the spirit and scope of the present invention as defined by the appended claims.

DETAILED DESCRIPTION OF THE EMBODIMENTS

Delivery of various chemical and biochemical factors to an implantation site is used to enhance tissue regeneration in a vicinity of the site, promoting integration of an implant with host tissue. Delivery of exogenous factors, however, introduces added complexity to the regeneration process. The method described herein enables the use of surface treatment of an implant to enhance the manufacture and release of cellular products by cells coupled to the implant. In this way, products synthesized by cells in situ may be used to regulate and to enhance tissue regeneration at an implantation site. Production and delivery of factors in situ to specific host sites may modify the need for delivery of exogenous factors.

Embodiments presented herein generally relate to a method of preparing an implant for use in biological/biomedical applications. The implant is formed from a substrate that is subjected to a gas-plasma treatment. In an embodiment, the substrate may be exposed to living cells, such that a portion of the living cells are coupled to the treated substrate. Gas-plasma treatment of the substrate, according to the embodiments described herein, enhance the release of cellular products by cells coupled to the substrate. As used herein, the term "implant" includes planar and nonplanar solids having a regular or an irregular shape. Exposing the substrate to living cells may be accomplished by placing unattached living cells on the substrate or placing the substrate in media containing living cells. Alternatively, the substrate may be exposed to living cells when the implant is placed in contact with host tissue. Living cells that are coupled to a substrate may be physically attached to or in physical contact with the substrate. Alternatively, living cells may be chemically coupled to a substrate. Living cells that are chemically coupled to a substrate may exhibit cellular activity in response to properties of the substrate or in response to a cell influenced by the substrate.

Examples of medical implants include, but are not limited to, tissue scaffolds, bone implants, cartilage implants, implantable drug or medication delivery systems, artificial skin, skin grafts, bone regeneration fillers, prostheses, and other attachable or implantable implants designed to facilitate tissue or organ regeneration, repair, reconstruction, and/or growth. The term "implant" may also refer to articles for other uses including, but not limited to, cell culturing and other biological and biomedical applications.

Implants may be composed of biocompatible materials including, but not limited to, metals, ceramics, and polymers. An implant may be substantially solid throughout, or at least a portion of an implant may be porous and/or permeable. In an embodiment, an implant may be pre-cast into a desired shape to fit a specific application. In another embodiment, an implant may be cut or stamped from planar or nonplanar solids, or the like, in shapes including, but not limited to, plates, disks, and cylindrical or conical plugs. In an embodiment, a shape of an implant may be modified as desired prior to gas-plasma treatment. In another embodiment, a shape of an implant may be modified as desired following gas-plasma treatment.

In biological/biomedical applications, implants may be advantageously composed of biocompatible polymers. Bioresorbable polymers are a class of biocompatible polymers that are eroded by cellular action and/or are biodegradable by action of non-living body fluid components. Bioresorbable polymers may be resorbed into host tissue over time. General examples of bioresorbable polymers include, but are not limited to, polyesters, polyamides, polypeptides, polyfumarates, polysaccharides, polylactides, polyglycolides, polycaprolactones, polyanhydrides, polyamides, polyurethanes, polyesteramides, polyorthoesters, polydioxanones, polyacetals, polyketals, polycarbonates, polyorthocarbonates, polyphosphazenes, polyhydroxybutyrates, polyhydroxyvalerates, polyalkylene oxalates, polyalkylene succinates, poly(malic acid), poly(amino acids), poly(methyl vinyl ether), poly(maleic anhydride), chitin, chitosan, and copolymers, terpolymers, or higher poly-monomer polymers thereof or combinations or mixtures thereof. Polymers that are degraded by hydrolysis may be advantageous.

Examples of bioresorbable polymers include poly(DL-lactic acid) (DL-PLA), poly(L-lactic acid) (L-PLA), poly(1-lactic acid) (P1LA), poly(glycolic acid) (PGA), poly(DL-lactic-co-glycolic acid) (PLG), and combinations, mixtures or blends thereof. For PLG, the co-monomer (lactide:glycolide) ratios may be between about 100:0 and about 50:50 lactic acid to glycolic acid. In an embodiment, the co-monomer ratios are between about 85:15 and about 50:50 lactic acid to glycolic acid. Blends of PLA with PLG may also be used to prepare implants. The degradation products of these polymers are low molecular weight compounds, such as lactic acid and glycolic acid, which enter into normal metabolic pathways. Furthermore, copolymers of PLG offer the advantage of a large range of degradation rates from a few days to a few years, depending on the copolymer ratio of lactic acid to glycolic acid.

Figure 1B:
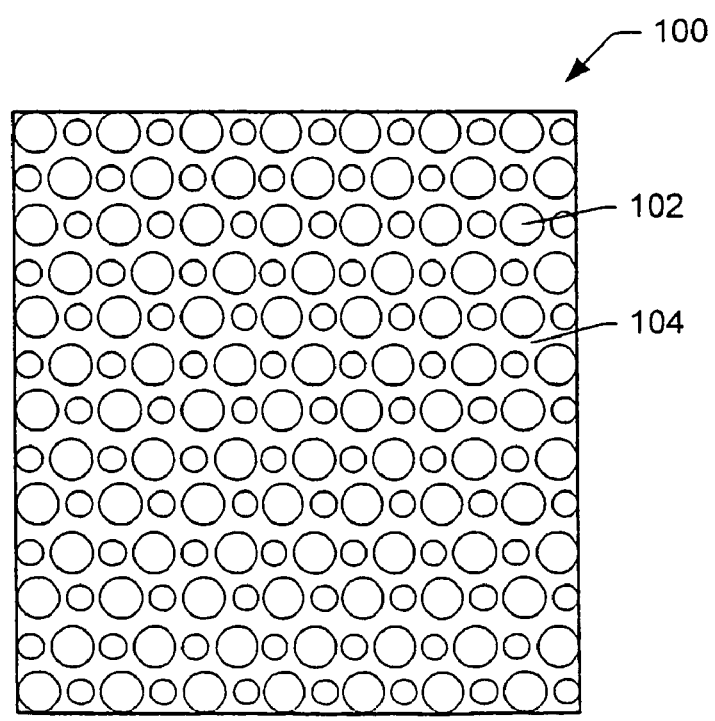

In an embodiment, three-dimensional bioresorbable DL-PLA polymer scaffolds may be fabricated using a vibrating particle technique described in U.S. Pat. Nos. 6,187,329 and 6,255,359 to Agrawal et al., both of which are incorporated by reference as if fully set forth herein. As used herein, the term "scaffold" means a three-dimensional matrix characterized by permeability and porosity that may be uniform or nonuniform. Scaffolds may be made of materials including, but not limited to, tubular, fibrous, and woven polymers. Other starting material configurations suitable for scaffold fabrication include woven or knitted items, micro-or-nano-spheres (i.e., fullerenes), micro- or nano-tubes, cobweb-like configurations, or foams/sponge-like forms. FIGS. 1A and 1B depict cross-sectional views of embodiments of scaffold 100. The circles in FIGS. 1A and 1B represent pores 102 in substrate 104. FIG. 1A is a cross-sectional view of a substantially uniform, highly permeable and/or porous scaffold. FIG. 1B is a cross-sectional view of a substantially uniform, highly permeable and/or porous scaffold having different pore sizes.

To enhance biodegradation of polymers used in biological applications, an implant may also include one or more enzymes to facilitate the biodegradation of the polymers used in the composition. Such enzymes include, but are not limited to, proteinase K, bromelaine, pronase E, cellulase, destranase, elastase, plasmin streptokinase, trypsin, chymotrypsin, papain, chymopapain, collagenase, chlostridopeptidase A, ficin, carboxypeptidase A, pectinase, pectinesterase, oxidoreductases, and oxidases. An appropriate amount of such a degradation enhancing agent may be used to regulate the lifetime of an implant. In various embodiments, implants may further contain other materials such as fillers that may improve polymer strength, materials that may aid in degradation, materials that may retard degradation such as antioxidants or anti-ozonants, biologically active agents, colorants, chromophores, light-activated (fluorescent or phosphorescent) tags, or any other material that may alter or change the property of the compositions.

Bioactive agents may be added to implants to provide biological, physiological, or therapeutic effects. Such agents may be incorporated into implants before gas-plasma treatment or applied to implants after gas-plasma treatment by dip or spray application or the like. Agents may be chemically or ionically bonded to substrate sites. Agents applied to bioresorbable implants may be released during biodegradation of the implant. Bioactive agents can be added to implants used as implants, for example, to enhance cell growth and tissue regeneration, act for birth control, or to cause nerve stimulation or bone growth.

Gas plasmas are created when energy sufficient to ionize atoms and/or molecules in a reactive gas causes ionization and subsequent generation of free electrons, photons, free radicals, and ionic species. Unlike distinct phase changes in other states of matter, transition of a gas or vapor from an unexcited, electrically stable state to an ionized plasma state generally occurs through a continuous process. The excitation energy supplied to a gas to form a plasma can originate from electrical discharges, direct currents, radio frequencies, microwaves, or other forms of electromagnetic radiation.

Gas-plasma techniques for modifying the surface characteristics of many materials are known. Specific applications for surface modified materials have been described for both microcircuit and medical implant device technology. In the medical implant industry, the use of plasma treatment of materials has generally focused on surface conditioning. U.S. Pat. Nos. 3,814,983; 4,929,319; 4,948,628; 5,055,316; 5,080,924; 5,084,151; 5,217,743; 5,246,451; 5,260,093; 5,262,097; 5,364,662; 5,451,428; 5,476,509; 5,229,172; 5,236,563; and 5,543,019, all of which are incorporated by reference as if fully set forth herein, describe surface conditioning of medical implants and other devices by radio frequency (RF) gas plasmas.

Many gas-plasma treatment techniques use RF radiation to break surface polymer bonds. This process generates ions and free radicals, setting up favorable conditions for subsequent RF plasma-induced polymerization and grafting of monomers to a substrate as described in U.S. Pat. No. 5,080,924, which is incorporated by reference as if fully set forth herein. In another application, similar covalent bonding of polymeric biocompatible materials to intraocular lenses via RF plasma grafting was achieved, creating a microscopically smooth surface as described in U.S. Pat. No. 5,260,093, which is incorporated by reference as if fully set forth herein.

Gas-plasma treatment may take place in a chamber capable of sustaining a plasma at low pressures. A substrate in the chamber is exposed to the plasma. In an embodiment, a RF plasma may operate at a frequency between about 10 kHZ and about 100 GHz, between about 1 MHz and about 100 MHz, or between about 13 MHz and about 14 MHz. Inert and/or reactive gases may be used in gas-plasma treatment. Examples of inert gases include, but are not limited to, noble gases such as helium and argon. Examples of reactive gases include, but are not limited to, oxygen, water vapor, hydrogen peroxide vapor, hydrogen, nitrogen, ammonia, and mixtures thereof. In an embodiment, an internal pressure during the gas-plasma treatment may be from about $10^{-4}$ torr to about 100 torr, from about 0.01 torr to about 10 torr, or about 0.15 torr. In an embodiment, a temperature inside the plasma chamber may be less than about 50° C., between about 10° C. and about 40° C., or about 25° C.

Duration of a gas-plasma treatment, together with RF power, may determine the energy delivered to the plasma chamber during treatment. In an embodiment, duration of the gas-plasma treatment may be greater than about 1 minute to less than about 5 minutes, between about 2 minutes and about 4 minutes, or about 3 minutes. In an embodiment, the RF power may range between about 25 watts and about 250 watts, between about 40 watts and about 100 watts, or about 60 watts. In some embodiments, treatment duration and RF power may be selected such that the product of power in watts and treatment duration in seconds is equal to a supplied energy between about 2 kJ and about 20 kJ, between about 5 kJ and about 10 kJ, or about 7.5 kJ. For example, a three-minute treatment with a RF power of 100 watts delivers a supplied energy of 100 watts×180 seconds=18,000 J, or 18 kJ, to the plasma chamber during treatment. In some embodiments, the RF power and/or phase may be varied during treatment.

U.S. Pat. No. 6,033,582 to Lee et al. describes a reactive plasma etching process that modifies the surface of an implant such that the resulting roughness, porosity, and texture are optimized for application of a coating. Biodegradable polymers such as poly(lactic acid) and poly(glycolic) acid are etched with noble gas (e.g., helium or argon) RF plasma in the presence of a reactive gas such as water vapor, oxygen, or hydrogen. The resulting roughened surface is shown to promote cellular ingrowth and allow improved adhesion of bioactive coatings, such as proteins, antibiotics, and nucleic acids, typically chosen to promote appropriate physiological responses in a host. It is further described that textured surfaces may be conditioned for cell attachment through application of growth matrix materials or components. Suitable conditioning materials are applied through dip coating and drying, followed by application of cells either in vitro or in situ. A post-etch application of a growth-promoting interface such as collagen or poly-lysine is proposed to promote adhesion of endothelial cells.

Gas-plasma treatment may be applied, for example, to implants for diseased or impaired organs or implants used to grow whole, artificial organs. Starting materials for these implants or artificial organs are generally biocompatible and may be bioresorbable. Starting materials should provide appropriate structural integrity and support and should be able to withstand selected gas-plasma conditions. Once a substrate is treated, appropriate cell growth materials and processes may be applied to the implant.

Gas-plasma treatment may induce formation of free radicals on a substrate. In an embodiment, gas-plasma treatment with a reactive gas that includes oxygen may induce formation of oxide free radicals on a substrate. As shown below, parameters chosen for a gas-plasma treatment may influence relative density of free radicals formed on the substrate.

Electron spectroscopy for chemical analysis ("ESCA") data from three-dimensional plug-shaped DL-PLA implants (5 mm diameter×2 mm thick) were used to compare mass concentration percentages corresponding to carbon atoms in various bonding configurations, including C=O, C—O, C—C, and C—O—O bonds, where applicable. Table 1 shows the percentages of C=O, C—O, and C—C bonds in an untreated substrate. Tables 2-4 show data from substrates subjected to gas-plasma treatment with an RF setting of 100 watts, and RF frequency of 10-11 MHz, a vacuum of 100-200 mtorr., using oxygen as the reactive gas. Table 2 shows percentages of C=O, C—O, C—C, and C—O—O bonds on a substrate following a 1 minute gas-plasma treatment with a RF power of 100 watts (supplied energy=6 kJ). Table 3 shows percentages of C=O, C—O, C—C, and C—O—O bonds on a substrate following a 3 minute gas-plasma treatment with a RF power of 40 watts (supplied energy=7.2 kJ). Table 4 shows percentages of C=O, C—O, C—C, and C—O—O bonds on a substrate following a 3 minute gas-plasma treatment with a RF power of 100 watts (supplied energy=18 kJ).

TABLE 1

Untreated

| Peak | Position (eV) | Mass Concentration % |
|---|---|---|
| C=O | 287.020 | 33.35 |
| C—O | 284.919 | 33.33 |
| C—C | 282.946 | 33.32 |

TABLE 2

Gas-plasma treated: 1 minute, 100 watts

| Peak | Position (eV) | Mass Concentration % |
|---|---|---|
| C=O | 282.843 | 31.47 |
| C—O | 284.748 | 34.59 |
| C—C | 286.851 | 30.45 |
| C—O—O | 287.800 | 3.49 |

TABLE 3

Gas-plasma treated: 3 minutes, 40 watts

| Peak | Position (eV) | Mass Concentration % |
|---|---|---|
| C=O | 286.941 | 39.12 |
| C—C | 284.802 | 31.77 |
| C—C | 282.907 | 22.70 |
| C—O—O | 288.797 | 6.41 |

TABLE 4

Gas-plasma treated 3 minutes, 100 watts

| Peak | Position (eV) | Mass Concentration % |
|---|---|---|
| C=O | 282.847 | 37.88 |
| C—O | 284.712 | 32.48 |
| C—C | 286.946 | 29.64 |

Data from the untreated substrate in Table 1 suggest that C=O, C—O, and C—C bonds are present in approximately equal numbers, with each bond type corresponding to approximately one-third of the carbon-containing surface bonds. Data from Table 2 for a substrate treated at a RF power of 100 watts for 1 minute suggest that gas-plasma treatment induced the formation of oxide radicals, with relative occurrences of C=O, C—O, C—C, and C—O—O bonds measured as 31.47%, 34.59%, 30.45%, and 3.49%, respectively. Data from Table 3 for a substrate treated at a RF power of 40 watts for 3 minutes suggest that gas-plasma treatment induced an even greater formation of oxide radicals, with relative occurrences of C=O, C—O, C—C, and C—O—O bonds measured as 39.12%, 31.77%, 22.70%, and 6.41%, respectively. Thus, the relative percentage of oxide radicals is almost twice as high for a 40 watt, 3 minute gas-plasma treatment than for a 100 watt, 1 minute gas-plasma treatment. Data from Table 4, with relative occurrences of C=O, C—O, and C—C bonds measured as 31.47%, 34.59%, and 30.45%, respectively, suggest that treatment at a RF power of 100 watts for 3 minutes does not promote formation of oxide radicals.

Gas-plasma treatment may cause a hydrophobic substrate to become more hydrophilic. As used herein, the term "hydrophilic" means having a tendency to bind water. The term "hydrophobic" is used herein to mean having a tendency to repel water. A more hydrophilic substrate may promote cellular adhesion and proliferation. In an embodiment, a gas-plasma treated substrate may be exposed to living cells, such that a portion of the living cells become coupled to the substrate. Examples of cells that may be coupled to treated substrates include, but are not limited to, endothelial cells, muscle cells, myocardial cells, and epithelial cells. In an embodiment, the endothelial cells may be human aortic endothelial cells (HAECs).

Living cells coupled to a gas-plasma treated substrate may produce and release more of a cellular product than cells coupled to an untreated substrate. Such cellular products include, but are not limited to, proteins and nucleic acids. In some embodiments, living cells coupled to a gas-plasma treated substrate produce and release more β-tubulin than cells coupled to an untreated substrate. β-tubulin is a protein that may correlate with cell proliferation as well as increased expression of other cellular products, such as growth factors. Examples of growth factors include, but are not limited to, colony stimulating factor, epidermal growth factor (EGF), erthyropoietin, fibroblast growth factor, neural growth factor, human growth hormone (HGH), platelet derived growth factor (PDGF), insulin-like growth factor (ILGF), fibronectin (FN), endothelial cell growth factor (ECGF), vascular endothelial growth factor (VEGF), cementum attachment extracts (CAE), basic fibroblast growth factor (bFGF), periodontal ligament cell growth factor (PDGF), epidermal growth factor (EGF), protein growth factor interleukin-1 (IL-1), transforming growth factor (TGF beta-2), human alpha thrombin (HAT), osteoinductive factor (OIF), and bone morphogenic protein (BMP), and platelet-endothelial cell adhesion molecule-1 (PECAM-1).

In an embodiment, living cells coupled to a gas-plasma treated substrate may produce more VEGF than living cells coupled to an untreated substrate. VEGF regulates endothelial cell growth and new blood vessel formation (angiogenesis). VEGF is capable of influencing the expression of other cellular products.

Figure 2:
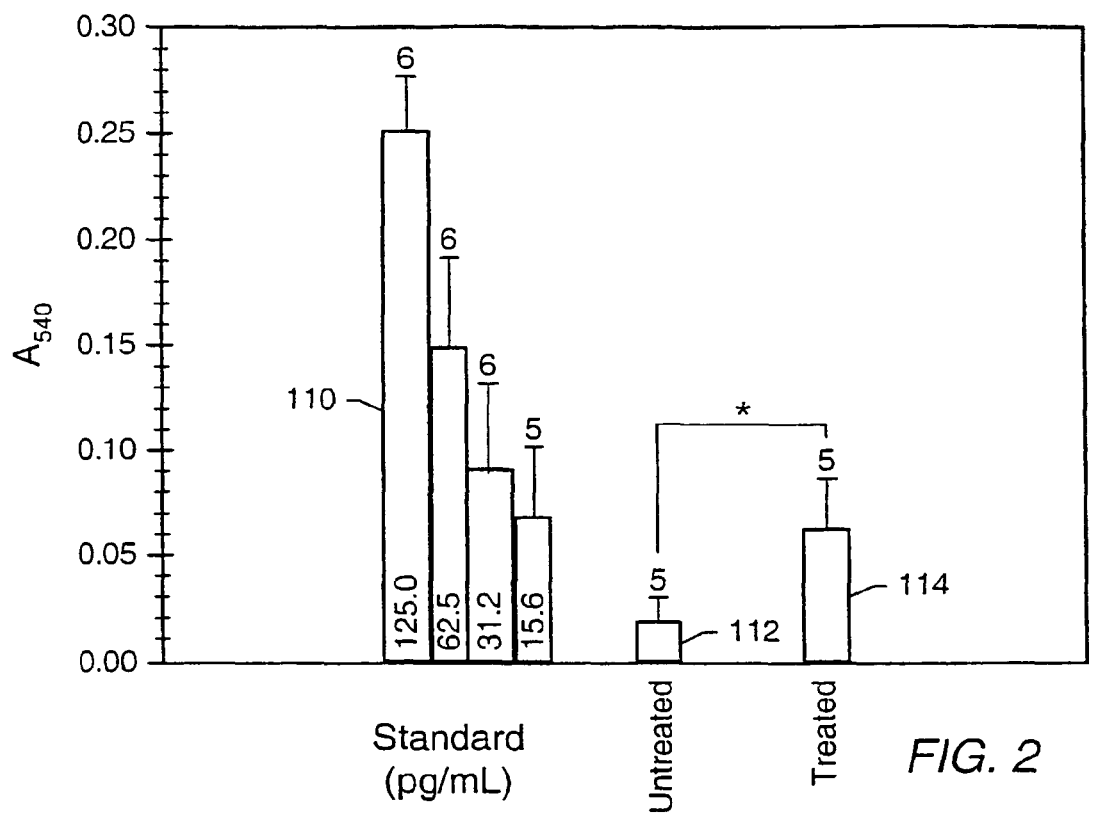
FIG. 2 is a histogram that shows VEGF absorbance for standard solutions and for VEGF amounts released by HAECs coupled to treated and untreated implants in vitro.

FIG. 2 is a histogram that shows mean absorbance (540 nm) ±standard deviations for VEGF standards 110 ranging from 15.6 to 125.0 pg/mL. Absorbance measurements for the VEGF standards were used to quantify an amount of VEGF released into the media from an in vitro study of HAECs incubated for 10 days near and within untreated and oxygen gas-plasma treated three-dimensional DL-PLA implants. VEGF levels released by HAECs into the media were higher (statistical significance p=0.016) for the treated implants 112 (range: 15.6-34 pg/mL) than for the untreated implants 114 (range: ≦15.6 pg/mL). After 18 days, HAECs within treated implants expressed higher VEGF intensities. Experimental VEGF quantities were determined using an enzyme-linked immunosorbant assay ("ELISA": R&D Systems; Minneapolis, Minn.).

In an embodiment, living cells coupled to a gas-plasma treated substrate may produce more PECAM-1 than living cells coupled to an untreated substrate of the same initial composition as the treated substrate. PECAM-1 is a growth factor influenced by VEGF that promotes cellular migration, survival, and replication.

Levels of PECAM-1 were investigated qualitatively in the in vitro study documented in FIG. 2. By 18 days, PECAM-1 within HAECs incubated within gas-plasma treated implants was heavily expressed throughout the cytoplasm and along the cytoskeleton of closely aligned and interconnecting cells. Migrating HAECs in untreated implants exhibited inferior and diffuse cytoplasmic PECAM-1 expression.

In an embodiment, free radicals on implant surfaces may simulate in vivo vascular injury, thereby promoting endothelial cell activation and induction of blood vessel formation, or angiogenesis. Angiogenesis was documented in an in vivo study of oxygen gas-plasma treated three-dimensional DL-PLA scaffolds above the omentum of nude mice. (The omentum is a fold of membrane extending from the stomach to adjacent organs in the abdominal cavity.) Visible vessels (>500 μm) were scored based on distance from the implants by two blinded observers. The grading system for the development of new vessels was:

Grade 1: Vessels seen on the implant.
Grade 2: Vessels seen on the implant and outside the implant (<5 mm).
Grade 3: Vessels seen on the implant and outside the implant (5-10 mm).
Grade 4: Vessels seen on the implant and outside the implant (>10 mm).

Figure 3:
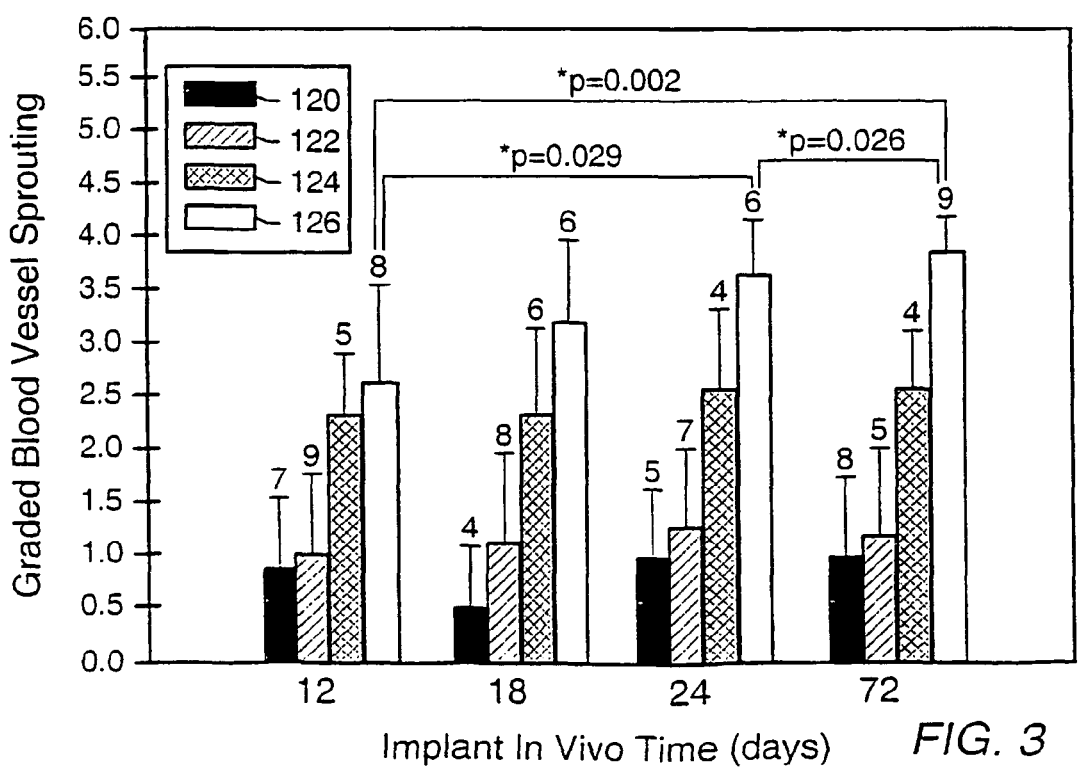
FIG. 3 shows graded blood vessel sprouting versus days in vivo for treated and untreated implants.

FIG. 3 shows mean graded blood vessel sprouting versus days ±standard deviation in vivo for untreated implants not exposed to HAECs 120, untreated implants exposed to HAECs 122, treated implants not exposed to HAECs 124, and treated implants exposed to HAECs 126.

An initial angiogenic response, or development of blood vessels, is noted for all the implants. More extensive blood vessel development is seen in the case of treated implants. The omentum and/or the skin of the mice with treated implants revealed angiogenesis that started early (12 days) and persisted throughout the experiment (72 days). There was a progressive increase in the grading between days 12 and 72 in the treated implants exposed to HAECs 126 and a steady high scoring in the treated implants not exposed to HAECs 124. The untreated implant groups showed less vessel formation with a maximum average grade of 1.5 for the untreated implants exposed to HAECs 122 and a maximum average grade of 1.2 for the untreated implants not exposed to HAECs 120.

A statistically significant difference is seen between the mice in the treated groups and untreated groups at all measured intervals (12, 18, 24, and 72 days). The difference is most noticeable between the mice with treated implants exposed to HAECs 126 and those with untreated implants not exposed to HAECs 120. The mice with untreated implants exposed to HAECs 122 showed slightly enhanced angiogenesis compared to the untreated implants not exposed to HAECs 120. The increase in the size of the vessels for the untreated implants exposed to HAECs 122 relative to the untreated implants not exposed to HAECs 120, however, was not statistically significant. The increase in blood vessel sprouting over time for treated implants exposed to HAECs 126 is statistically significant, as indicated by p values ranging from 0.029 to 0.002.

In the same study, VEGF expression at day 18 was more evident in the vessels in and around the implants in mice with treated implants than in mice with untreated implants. PECAM-1 expression was evaluated qualitatively at day 18 in the omentum of mice with treated and untreated implants. A substantial proportion of the mice with treated implants showed evidence of PECAM-1 expression in tissues surrounding the implants. Untreated implants revealed less intense PECAM-1 expression.

As a bioresorbable implant, such as a DL-PLA implant, begins to degrade within a host, an injury stimulus of substrate free radicals may diminish. As a result, the production of angiogenic growth factors such as VEGF may taper off. This internal control may prevent the formation of vascular tumors. In addition, the local release of growth factors in the vicinity of the implant may reduce the need for delivery of exogenous growth factors.

EXAMPLE 1

The following example describes coupling of HAECs to L-PLA films in vitro.

Culture: HAECs (Clonetics 1998, Passages 5-8: Cambrex Corporation; East Rutherford, N.J.) were seeded using basal MCDB-131 (Sigma; St. Louis, Mo.) media. The chemically defined MCDB-131 was supplemented with 1 μg/mL hydrocortisone (HC: Sigma), 250 ng/mL basic fibroblast growth factor (bFGF: PeproTech; Rocky Hill, N.J.), 1 μg/mL epidermal growth factor (EGF: Gibco; Rockville, Md.), 100 I.U. penicillin/streptomycin (P/S; Cellgro: Herndon, Va.), and 10% iron-supplemented bovine calf serum (BCS; Hyclone: Logan, Utah). The supplemented MCDB-131 media was buffered with sodium bicarbonate and HEPES, free acid. The media had an average beginning pH of 7.35 and an osmolarity of 324 mOsm at 22° C. Prior to seeding, HAECs were treated with 0.5% trypsin plus 0.53 mM EDTA (Gibco). HAECs were collected by centrifugation, re-suspended in supplemented MCDB-131, and then seeded onto the center of bioresorbable polymer films, prepared as described below. The endothelial cultures were grown in a 37° C. humidified 5% $CO_2$/95% $O_2$ incubator. Coupled HAECs were fed every two to three days with supplemented MCDB-131 media.

Bioresorbable polymer films: L-PLA films were prepared by dissolving the dry L-PLA (MW 450 kD; Birmingham Polymers, Inc.: Birmingham, Ala.) in methylene chloride. The dissolved L-PLA was poured onto a glass mold. A glass recrystallization dish was placed over the solution in the mold to control airflow and evaporation rate at 4° C. After the solvent evaporated, the films were rinsed with sterile distilled water and removed from the glass plates. 15 mm-diameter circles were extracted from the L-PLA films using a metal punch. Gas-plasma treatment was performed using the STERRAD sterilization technology (Advanced Sterilization Products; Irvine, Calif.), which involved the combined use of hydrogen peroxide and low-temperature gas plasma. The process temperature did not exceed 50° C. and treatment occurred in a low moisture environment.

The treated films showed greater endothelial proliferation than untreated films, as indicated by increased β-tubulin expression.

EXAMPLE 2

The following example describes coupling of HAECs to three-dimensional bioresorbable DL-PLA implants in vitro.

Culture: HAECs (Passages 4-7) were seeded at sub-confluent densities using basal MCDB-131 (Sigma) media supplemented with 1 μg/mL hydrocortisone (HC: Sigma), 250 ng/mL basic fibroblast growth factor (bFGF: PeproTech), 1 μg/mL epidermal growth factor (EGF: Gibco), 100 I.U. penicillin/streptomycin (P/S: Cellgro), and 10% iron-supplemented bovine calf serum (BCS; Hyclone) buffered with sodium bicarbonate and HEPES, free acid (pH 7.35; 324 mOsm). HAECs were treated with 0.5% trypsin plus 0.53 mM EDTA (Gibco), collected by centrifugation, re-suspended in supplemented MCDB-131, and then seeded onto the center of bioresorbable DL-PLA implants housed in 96-well plates (Corning; Corning, N.Y.). When seeded onto implants made as described below, the media was switched to RPMI 1640 (Cellgro) with the same supplements and 10% BCS (pH 7.35; 280 mOsm). Endothelial cultures were grown in a 37° C. humidified 5% $CO_2$/95% $O_2$ incubator (VWR; West Chester, Pa.). HAECs were fed every two to three days during the three to eighteen days of incubation.

Bioresorbable polymer implants: Using sterile techniques, three-dimensional substrates were fabricated using DL-PLA with an inherent viscosity of 0.63 dL/g (Birmingham Polymers, Inc.). Implants were fabricated using a vibrating particle technique described in U.S. Pat. Nos. 6,187,329 and 6,255,359 to Agrawal et al., resulting in highly porous and permeable plug-shaped implants (5 mm diameter×2 mm thick). Implants were treated using a RF (13.18 MHz) glow discharge of oxygen in a 2 ¾ inch glass chamber (Harrick Plasma Cleaner: Harrick Scientific Corporation; Ossining, N.Y.). The internal pressure was 0.15 torr. The process temperature did not exceed 50° C., and treatment occurred in a low-moisture environment.

VEGF expression was greater in the wells of treated implants than the wells of untreated implants. VEGF levels outside the treated implants were also elevated. PECAM-1 within HAECs incubated within gas-plasma treated implants was heavily expressed throughout the cytoplasm and along the cytoskeleton of closely aligned and interconnecting cells. Migrating HAECs in untreated implants exhibited inferior and diffuse cytoplasmic PECAM-1 expression.

EXAMPLE 3

The following example describes coupling of HAECs to three-dimensional DL-PLA implants for use as implants in nude mice.

Three-dimensional scaffolds were fabricated using a DL-PLA polymer with an inherent viscosity of 0.63 dl/g (Birmingham Polymers, Inc.). Scaffolds were fabricated using a vibrating particle technique described in U.S. Pat. Nos. 6,187, 329 and 6,255,359 to Agrawal et al., resulting in highly porous and permeable scaffolds. Implanted scaffolds (5 mm diameter×2 mm thick) were cut from the composite using a punch, immersed in water for 48 hours to remove the NaCl, and dried in a vacuum. All materials and instruments used for the scaffold fabrication were sterilized beforehand.

Implants were gas-plasma treated using a RF glow discharge of oxygen (Harrick Plasma Cleaner) in a 2¾ inch glass chamber at a frequency of 13.18 MHz, at a power of 100 Watts for 3 minutes, and at an internal pressure of 0.15 torr. The process temperature did not exceed 50° C. and treatment occurred in a low-moisture environment.

$3 \times 10^4$ HAECs (Passages 5-8, BioWhittaker: Walkersville, Md.) were allowed to attach to each free floating implant using RPMI 1640 supplemented with 1 µg/mL hydrocortisone (Sigma), 250 ng/mL bFGF (PeproTech), 1 µg/mL epidermal growth factor (Gibco); 100 I.U. penicillin/streptomycin (Cellgro) and 10% BCS (Hyclone). Media was replaced every 2-3 days. 2-4 hours prior to implantation, near confluent 6-day endothelialized implants were switched to media supplemented as listed above without serum.

Results: Formation of new vessels was seen in abdominal skin when mice were alive. Formation of new vessels was seen in the peritoneum, abdominal skin, or both postmortem. Mice in each group showed implant-induced angiogenesis. The angiogenic response was more noticeable, however, in mice with treated implants. VEGF and PECAM-1 expression were greater in and around treated implants. β-tubulin expression was enhanced in HAECs located in the treated implants.

EXAMPLE 4

The following example describes coupling of HAECs to three-dimensional DL-PLA implants used as implants in a nude mouse omental model.

Culture: HAECs (BioWhittaker) were seeded with $3 \times 10^4$ HAECs using RPMI 1640 supplemented with 1 mg/mL hydrocortisone (HC: Sigma), 250 ug/mL basic fibroblast growth factor (bFGF: PeproTech), 1 ug/mL epidermal growth factor (EGF: Gibco), 100 I.U. penicillin/streptomycin (P/S: Cellgro), and 10% iron-supplemented bovine calf serum (BCS: Hyclone). Supplemented RPMI 1640 was replaced every 2-3 days.

Bioresorbable polymer implant: Three-dimensional scaffolds were fabricated using DL-PLA with an inherent viscosity of 0.63 dl/g (Birmingham Polymers, Inc.). Scaffolds were fabricated using a vibrating particle technique described in U.S. Pat. Nos. 6,187,329 and 6,255,359 to Agrawal et al., resulting in highly porous and permeable scaffolds. Briefly, 0.35 gm of DL-PLA was dissolved in 3.25 ml of pure acetone under continuous stirring. Approximately 2.25 gm of sodium chloride (NaCl) particles (250 µm≦size≦500 mm) were spread evenly at the bottom of a Teflon™ mold with a rectangular well cavity (33×20×15 mm). Next, the polymer solution was poured onto the salt in an even fashion. The mold was then placed under continuous airflow conditions and vibrated using a Thermolyne Maxi Mix II (Barnstead/Thermolyne; Dubuque, IA) for 8 minutes. An additional 4.5 gm of salt were added during this period. The mold was continuously vibrated until the solvent evaporated, leaving behind a solid salt-polymer composite. This composite was placed in a heated vacuum at 45° C. and 5 torr for 24 hours. Disk-shaped scaffolds (5 mm diameter×2 mm thick) were cut from the composite using a punch, immersed in water for 48 hours to remove the NaCl, and dried in a vacuum. All materials and instruments used for the scaffold fabrication were sterilized beforehand.

Implants were gas-plasma treated using a RF glow discharge of oxygen (Harrick Plasma Cleaner) in a 2¾ inch glass chamber at a frequency of 13.18 MHz, at a power of 100 Watts for 3 minutes, and at an internal pressure of 0.15 torr. The process temperature did not exceed 50° C. and treatment occurred in a low-moisture environment.

Results: Qualitative analysis of implants revealed enhanced local expression of VEGF and PECAM-1 in and around the treated implants. There was also a more organized local new blood vessel sprouting in the vicinity of treated implants.

What is claimed is:
1. An implant prepared by a process comprising:
subjecting a bioresorbable polymeric substrate to a gas-plasma treatment, wherein the bioresorbable polymeric substrate comprises a polylactide polymeric material, wherein subjecting the substrate to the gas-plasma treatment comprises exposing the substrate to a reactive gas, wherein the reactive gas comprises oxygen, and wherein the supplied energy during the gas-plasma treatment is between about 5 kJ and about 10 kJ at a temperature of less than about 50 C, a pressure between about 0.01 torr and about 10 torr, and a discharge frequency between about 13 MHz and about 14 MHz, wherein the reactive gas comprises an oxygen content sufficient to provide oxide free radicals on the substrate when the substrate is subjected to the gas-plasma treatment; and exposing the substrate subjected to the gas-plasma treatment to living cells that produce vascular endothelial growth factor (VEGF), wherein a portion of the living cells that produce VEGF become coupled to the substrate; and wherein the living cells that produce VEGF coupled to the substrate subjected to the gas-plasma treatment produce more VEGF than living cells that produce VEGF when coupled to the substrate not subjected to the gas-plasma treatment.

2. A method of preparing an implant, comprising:

subjecting a bioresorbable polymeric substrate to a gas-plasma treatment, wherein the bioresorbable polymeric substrate comprises a polylactide polymeric material, wherein subjecting the substrate to the gas-plasma treatment comprises exposing the substrate to a reactive gas, wherein the reactive gas comprises oxygen, and wherein the supplied energy during the gas-plasma treatment is between about 5 kJ and about 10 kJ at a temperature of less than about 50 C, a pressure between about 0.01 torr and about 10 torr, and a discharge frequency between about 13 MHz and about 14 MHz, wherein the reactive gas comprises an oxygen content sufficient to provide oxide free radicals on the substrate when the substrate is subjected to the gas-plasma treatment; and exposing the substrate subjected to the gas-plasma treatment to living cells that produce vascular endothelial growth factor (VEGF), wherein a portion of the living cells that produce VEGF become coupled to the substrate; and wherein the living cells that produce VEGF coupled to the substrate subjected to the gas-plasma treatment produce more VEGF than the living cells that produce VEGF when coupled to the substrate not subjected to the gas-plasma treatment.

3. The method of claim 2, wherein the substrate comprises a three-dimensional matrix.

4. The method of claim 2, wherein the substrate comprises a planar solid.

5. The method of claim 2, wherein the substrate comprises a nonplanar solid.

6. The method of claim 2, wherein the implant is a medical implant.

7. The method of claim 2, wherein the reactive gas consists essentially of oxygen.

8. The method of claim 2, wherein the living cells comprise endothelial cells.

9. The method of claim 2, wherein the living cells comprise human aortic endothelial cells.

10. The method of claim 2, wherein the living cells comprise muscle cells.

11. The method of claim 2, wherein the living cells comprise myocardial cells.

12. The method of claim 2, wherein the living cells comprise epithelial cells.

* * * * *